United States Patent
Rooney et al.

(10) Patent No.: US 12,092,625 B2
(45) Date of Patent: Sep. 17, 2024

(54) PRECISION SITE CHARACTERIZATION USING DIGITAL TWIN

(71) Applicant: LandScan LLC, San Luis Obispo, CA (US)

(72) Inventors: Daniel James Rooney, Lake Oswego, OR (US); Stephen P Farrington, Gaysville, VT (US); Woody Guthrie Wallace, Madison, WI (US); Jeffrey W Dlott, Santa Cruz, CA (US)

(73) Assignee: LandScan LLC, San Luis Obispo, CA (US)

( * ) Notice: Subject to any disclaimer, the term of this patent is extended or adjusted under 35 U.S.C. 154(b) by 354 days.

(21) Appl. No.: 17/219,615

(22) Filed: Mar. 31, 2021

(65) Prior Publication Data
US 2022/0317107 A1 Oct. 6, 2022

(51) Int. Cl.
*G01N 33/24* (2006.01)

(52) U.S. Cl.
CPC .................................. *G01N 33/24* (2013.01)

(58) Field of Classification Search
CPC ...... G01N 33/24; G01N 21/251; G01V 11/00; G01V 8/02
See application file for complete search history.

(56) References Cited

U.S. PATENT DOCUMENTS

| | | | |
|---|---|---|---|
| 5,323,317 A * | 6/1994 | Hampton | B64G 1/66 702/3 |
| 6,647,799 B1 | 11/2003 | Hall et al. | |
| 6,834,550 B2 | 12/2004 | Andrade-Sanchez et al. | |
| 6,904,160 B2 | 6/2005 | Burgess | |
| 6,999,877 B1 | 2/2006 | Dyer et al. | |
| 8,195,682 B2 | 6/2012 | Fein et al. | |
| 8,494,726 B2 | 7/2013 | Aral | |
| 2003/0083819 A1* | 5/2003 | Rooney | G01V 11/00 703/5 |
| 2005/0150160 A1 | 7/2005 | Burns | |
| 2006/0158652 A1* | 7/2006 | Rooney | G01N 21/251 356/406 |
| 2008/0140431 A1 | 6/2008 | Anderson et al. | |
| 2010/0036696 A1 | 2/2010 | Lang et al. | |
| 2014/0084927 A1* | 3/2014 | Walsh | G01V 3/14 324/322 |
| 2016/0260021 A1 | 9/2016 | Marek | |
| 2019/0050948 A1 | 2/2019 | Abramson et al. | |
| 2019/0137653 A1* | 5/2019 | Starr | G01V 8/02 |
| 2020/0128721 A1 | 4/2020 | Aulbach et al. | |

* cited by examiner

*Primary Examiner* — Michael J Dalbo
*Assistant Examiner* — Kaleria Knox
(74) *Attorney, Agent, or Firm* — Downs Rachlin Martin PLLC

(57) ABSTRACT

Subject soils are classified using a sensing tool. By profiling each of a number of first locations that have a ground truth classification, using a deployed sensing tool, digital soil properties of new locations without ground truth classifications can be obtained to determine corresponding classifications for the new locations. This allows information related to classifications to be utilized for optimal use of the new locations.

19 Claims, 11 Drawing Sheets

PRECISION SITE CHARACTERIZATION USING DIGITAL TWIN

TECHNICAL FIELD

The present invention relates generally to a method, system, and computer program product for soil characterization. More particularly, the present invention relates to a method, system, and computer program product for classifying one or more soil properties in a geographic region.

BACKGROUND

The term property or properties is used herein to refer to obtained associations of soil conditions. The associations can be obtained by, for example, measuring, observing, deriving, inferring, aggregating, or predicting attributes/parameters of soil which attributes/parameters include, for example, physical, biological, chemical, electrical, optical, structural, spatial/temporal distributions, biogeochemical and biogeospatial conditions of soil. Soil survey or mapping is a process of classifying soil types and properties in a given area and geo-encoding such information. It is achieved by delineating natural bodies of soils, classifying and grouping the delineated soils into soil map units, and capturing soil property information for interpreting and depicting soil spatial distribution on a map. Information from soil surveys is publicly/privately available in the United States and other countries as images with closed boundaries or polygons each enclosing a geographic region or soil map unit and labeled with a numeric or letter label corresponding to specific subsurface properties of the geographic region.

Determining a soil map unit in which a geographical site is located allows one to obtain information about said site including, for example, soil composition for development assessment. For example, the information may be used by farmers and ranchers to determine whether a particular soil type is suited for crops or livestock and what type of soil management is required. Moreover, an engineer or architect may use the engineering properties of a soil to determine whether it is suitable for a certain type of construction.

The characteristics of a soil are recorded in order to survey said soil. Typically, a limited number of pedons, or a body of soil or pit with dimensions large enough to permit the study of individual soil horizons are obtained in a geographic region in order to define the boundaries of soil map units in said geographic region. Mapping the soil involves characterizing the pedons, associated plant communities, geology, landforms, and other features. The characterization is a manual characterization that describes the kinds and arrangements of soil horizons and their color, texture, size and shape of soil aggregates, kind and amount of rock fragments, distribution of plant roots, reaction, and other features that enable the classification and identification of soils.

After identifying and describing the soils and properties of landscape components, or natural bodies of soils, the components are correlated to a soil series or taxonomic class. A soil Series is the most detailed classification in the taxonomy. The World Reference Base and other national classification systems are used throughout the world. Each taxonomic class has a set of soil characteristics with precisely defined limits. The classes are used as a basis for comparison to classify soils systematically. Soil Taxonomy, the system of taxonomic classification used in the United States, is based mainly on the kind and character of soil properties and the arrangement of horizons within the profile As the number or letter of a soil map unit corresponds to a particular characteristic soil type and profile, many soil map units in a particular area may have identical labels. A table is used in a publicly available Soil Survey to link each soil map unit to one or more soil series names, and for each soil series name, the Soil Survey contains a textual description of a representative soil profile. A map unit can represent one or more soil series association as major or minor components. Some map units are complexes, which indicate that they may contain small areas of a high number of soil series. Some soil series are related geographically and may or may not be grouped into a single map unit.

SUMMARY

The illustrative embodiments provide a method, system and computer program product for soil classification. In an aspect herein, a method of classifying one or more soil properties in a geographic region is disclosed. The method includes: deploying a sensing tool, configured to obtain (generally referred to hereinafter to as detect, measure, infer and the like) values of one or more soil properties, with increasing depth, at one or more first locations within the geographic region, the one or more first locations being locations that each have a predefined classification; obtaining a first depth varying raw signal output from the sensing tool for each soil property of each of the one or more first locations; creating, for each of the one or more first locations, a first signature corresponding to the predefined classification in order to produce one or more first correspondence signatures; deploying the sensing tool to a second location that does not have an associated or correct predefined classification; obtaining one or more second depth varying raw signal outputs from the sensing tool for one or more of the soil properties of the second location; and, determining, responsive to the obtaining, by using the one or more second depth varying raw signal outputs or a second signature thereof, a corresponding classification for the second location based on the one or more first correspondence signatures and their predefined classifications. In one or more aspects herein said raw signals are calibrated values or measurements from sensors configured to provide engineering or scientific units of property values, such as resistivity, penetration force, Munsell color, etc.

In another aspect herein, the method includes one or more combinations of the following: (i) the predefined classification is a predefined reference soil series, (ii) the one or more soil properties is a subsurface property, (iii) the determining includes obtaining, for the second location, the second signature using the one or more second depth-varying raw signal outputs and using the second signature to compute a closest matching signature to the one or more first correspondence signatures, the corresponding classification for the second location being determined as the predefined reference soil series of said closest matching signature, (iv) the one or more correspondence signatures are stored in a database, (v) values of one or more soil properties are measured continuously in a given timeframe, e.g., 1 to 30 values of each property per second as the probe is penetrating the soil at a rate of, for example, approximately 20 (+/−5) mm per second, thereby producing sensor values approximately every 10 mm or less, (vi) the sensing tool is a multi-sensor penetrometer, (vii) the closest matching signature is computed by curve comparison, (viii) said predefined classification and the corresponding classification are a level of classification chosen from a Soil Taxonomy classification system.

In yet another aspect herein, another method of classifying one or more soil properties in a geographic region is disclosed. The method includes: deploying a sensing tool, configured to measure values of the one or more soil properties, with increasing depth, at a subject location within the geographic region; obtaining a depth varying raw signal output from the sensing tool for each of the one or more soil properties of the subject location; corresponding discretized signals of the depth varying raw signal output received from the sensing tool to one or more soil property values of a classification chart; and, determining a classification for the subject location by determining a classification that corresponds to the one or more soil property values.

Said another method may also include one or more combinations of the following: (i) the classification is a reference soil series, (ii) each discretized signal of the set of discretized signals is corresponded to a soil property value of the one or more soil property values, (iii) a measure of the central tendency, e.g., an average, of a cluster of discretized signals is corresponded to a soil property value of the one or more soil property values, (iv) the sensing tool is a multi-sensor penetrometer, (v) the classification chart is a digitized chart chosen from a group that includes, for example, a soil texture triangle, a Munsell soil color chart, a grain size chart, a geotechnical gauge, a sand gauge, a reactivity chart, and a diagnostic horizon depth chart. The classification chart may also be a chart of landscape position and geomorphic features. In an illustrative embodiment, a multidimensional database if generated, wherein the multi-dimensional database includes series, their horizons, characteristics of their horizons and the range of characteristics associated with each horizon for each series. Specifically, these include: Hue, Value, Chroma, Texture (really Sand, Clay), Rock Fragment content, Reaction (pH), Horizon Thickness, Depth to C horizon, Depth to carbonates (or other diagnostic horizons). Slope range, and landscape position, and geomorphic feature associations and the relationship between competing and geographically associated soils.

In an even further aspect, a system for classifying one or more soil properties in a geographic region is disclosed. The system includes at least one processor that is adapted to: deploy a sensing tool that measures change in the one or more soil properties with increasing depth, at one or more first locations within the geographic region, the one or more first locations being locations that each have a predefined classification; obtain a first depth varying raw signal output from the sensing tool for each soil property of each of the one or more first locations; create, for each of the one or more first locations, a first signature corresponding to the predefined classification in order to produce one or more first correspondence signatures; deploy the sensing tool to a second location that does not have an associated or correct predefined classification; obtain one or more second depth varying raw signal outputs from the sensing tool for one or more of the soil properties of the second location; and, determine, responsive to obtaining the one or more second depth varying raw signal outputs, by using the one or more second depth varying raw signal outputs or a second signature thereof, a corresponding classification for the second location based on the one or more first correspondence signatures and their predefined classifications. In the system, the predefined classification is a predefined reference soil series and the one or more soil properties is a subsurface property.

Another system for classifying one or more soil properties in a geographic region, is also envisioned. Said another system also includes at least one processor configured to: deploy a sensing tool that measures values of the one or more soil properties with increasing depth, at a subject location within the geographic region; obtain a depth varying raw signal output from the sensing tool for each of the one or more soil properties of the subject location; correspond discretized signals of the depth varying raw signal output received from the sensing tool to one or more soil property values of a classification chart; and determine a classification for the subject location by determining a classification that corresponds to the one or more soil property values. In this system, the classification may also be a reference soil series.

Even further, a non-transitory computer-readable medium is disclosed. The non-transitory computer-readable storage medium stores a program which, when executed by a computer system, causes the computer system to perform a procedure that includes: obtaining a first depth varying raw signal output from the sensing tool for each soil property of each of one or more first locations wherein a sensing tool is deployed, the sensing tool being configured to measure values of the one or more soil properties, with increasing depth, the one or more first locations being locations that each have a predefined classification; creating, for each of the one or more first locations, a first signature corresponding to the predefined classification in order to produce one or more first correspondence signatures; obtaining one or more second depth varying raw signal outputs from the sensing tool for one or more of the soil properties of a second location that does not have an associated or correct predefined classification; and, determining, responsive to the obtaining, by using the one or more second depth varying raw signal outputs or a second signature thereof, a corresponding classification for the second location based on the one or more first correspondence signatures and their predefined classifications.

Another non-transitory computer-readable stores a program which, when executed by a computer system, causes the computer system to perform a procedure comprising: obtaining a depth varying raw signal output from a sensing tool for each of one or more soil properties of a subject location where the sensing tool is deployed, the sensing tool being configured to measure values of the one or more soil properties, with increasing depth; corresponding discretized signals of the depth varying raw signal output received from the sensing tool to one or more soil property values of a classification chart; and determining a classification for the subject location by determining a classification that corresponds to the one or more soil property values.

BRIEF DESCRIPTION OF THE DRAWINGS

Certain novel features believed characteristic of the invention are set forth in the appended claims. The invention itself, however, as well as a preferred mode of use, further objectives and advantages thereof, will best be understood by reference to the following detailed description of the illustrative embodiments when read in conjunction with the accompanying drawings, wherein:

DETAILED DESCRIPTION

Figure 1:
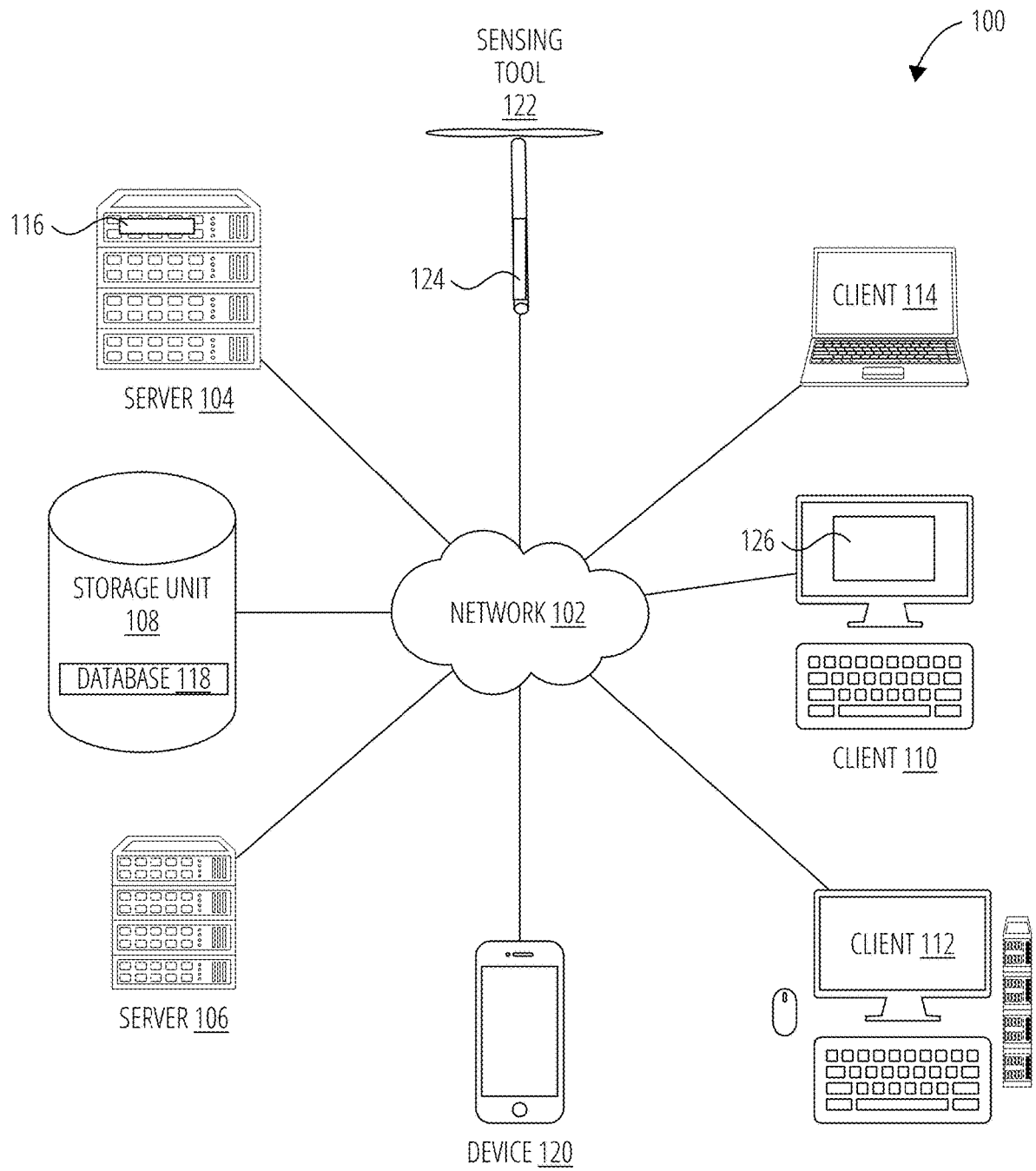
FIG. 1 depicts a block diagram of a network of data processing systems in which illustrative embodiments may be implemented.

The illustrative embodiments recognize that boundaries for the soil map units are identified somewhat heuristically by using judgements based on observable characteristics of significant natural bodies of soil in the survey area/vicinity of the pedon. An ensuing problem therefore is that, since only a limited number of pedons can be studied, for example, one or a few pedons in a soil map units, creation of the boundaries of the soil map units is prone to human error with some boundaries being too far away from a studied pedon and thus not configured to capture actual changes in soil properties with increasing distance away from said pedon. Moreover new/future studies of soils for potential development sites and for comparison to "ground truth" surveys are also prone to human error due to a potential to mischaracterize visual properties of soil differently that of trained scientists.

The illustrative embodiments further recognize that there is a need to classify soils in a digital fashion to eliminate or substantially eliminate human error and increase speed of mapping. For example, an individual might gain ownership of an unmapped or loosely mapped site for agricultural development. Without the ability to accurately determine a reference soil series representative of each of a plurality of locations on the site, said individual would have to rely on a predefined reference soil series from a possibly outdated soil mapping or a mapping that does not account for actual spatial soil variability on the site. Information garnered from the predefined reference soil series may thus be only applicable to locations on the site that are in close proximity to a corresponding pit used in the original mapping.

Classifying soils in a computerized/digital fashion enables actual soil composition and related information to be obtained and a larger number of locations to be mapped in a relatively short period compared to the number of locations mapped using conventional means. Responsive to deploying a sensing tool, such as a penetrometer, configured to automatically measure and/or relay a plurality of soil properties with increasing depth at a location, said properties are usable to generate a determination of a soil series representative of said location in a relatively short period of time compared to manual conventional methods. A plurality of other locations can thereafter or concurrently be surveyed and mapped in, for example, a few minutes.

In addition, many presently-available sensing tools include means for measuring soil properties. However said presently-available sensing tools simply only measure soil properties at certain depths in a soil that is being surveyed, resulting in large gaps in individual measurements as well as measurements that are wrongly attributed to all parts of a soil horizon in a pit instead of being attributed to the location of the pit at which said measurements were taken.

Moreover, many soil scientists presently collect data manually when classifying a soil and do not include a provision to relay said collected data in a networked fashion. Instead, measurements are manually taken by an operator through the reading and manual recording of displayed measurement values.

The illustrative embodiments recognize that the presently available tools or solutions do not address these needs or provide adequate solutions for these needs. The illustrative embodiments used to describe the invention generally address and solve the above-described problems and other problems related to classifying one or more subsurface properties in a geographic region.

An embodiment can be implemented as a software and/or hardware application. The application implementing an embodiment can be configured as a modification of a classification system, as a separate application that operates in conjunction with an existing classification system, a standalone application, or some combination thereof.

Illustrative embodiments thus provide a method by which a soil that is newly characterized in situ using a sensing tool, is classified as being functionally equivalent to (e.g., "matching" or "snapping" to) a soil previously characterized by the same or alternate means that is described in an existing database. This is achieved by finding a nearest neighbor in the database in parameters space wherein the parameters comprising the space are, for example, raw signal values, discretized signal values, quantitative and/or qualitative interpretations of signal values, or a combination thereof. Thus, consider that a first soil is functionally equivalent for purposes of agricultural, silvacultural, or other management decision making to a second soil selected from among a defined set of standardized, pre-characterized or pre-defined soils recorded in a database representing a soil taxonomy system. The selection of the second soil to which the first soil is functionally equivalent is performed on the basis of one or more of the second soil's properties being the "most similar" (or at least above a defined threshold), among the set of possible second soils, to one or more of the first soil's properties as determined in situ using the sensing tool. The first soil is thus "snapped" to the second soil that is the nearest neighbor in soil property space among all neighbors represented in the taxonomic system or pre-defined database. The determination of nearest neighbor in the soil property space is made on the basis of several methods of evaluating similarity or distance applicable to any vector representation of values in a generalized parameter space, such as but not limited to, Euclidean distance, Manhattan distance, Chebychev distance, cosine distance, Jacquard distance, Sorensen-Dice distance, and Hamming distance, with different distance metrics being more of less appropriate depending on the combination and nature of the properties in the parameter space. Other measures of similarity or distance could also be used, including but not limited to hybrid combinations of the measures named above. For property data in near-continuous profile such as raw sensor values, cross-correlation, dynamic time warping (DTW), and Fréchet distance are some additional distance metrics from among possible metrics that can also be useful for identifying the nearest neighbor second soil.

Particularly, some illustrative embodiments provide a method that classifies one or more soil properties including subsurface properties in a geographic region. Though subsurface properties are generally used for classification herein, this is not intended to be limiting and soil properties obtained from ground surfaces or surfaces above the ground are possible. The classification may be achieved by deploying a sensing tool at one or more first locations within the geographic region. The one or more first locations have a predefined reference soil series according to a Soil Survey. The sensing tool is configured to continuously detect/measure values of the one or more subsurface properties, with increasing depth. Measurements are automatically obtained from the sensing tool and measurement signatures created for each location. The measurement signatures correspond to the respective reference soil series. Since each location has a predefined ground truth reference soil series, the corresponded signatures establish a calibration for the sensing tool against which future measurements may be compared. The sensing tool is thereafter deployed at a new location that has not been previously mapped, or a location whose soil composition has changed with time. By obtaining a corresponding signature for the new location and comparing it to a database of calibration signatures, an actual reference soil series can be computed for the new location. Various comparison methods including curve matching algorithms, shape matching algorithms, and analyses that provide at least a threshold degree of a statistical confidence of matching can be employed. Example shape matching algorithms that may be employed match shapes of sensor response versus depth on the basis of similarity measures and may include but are not limited to Euclidean distance, dynamic time warping (DTW), longest common subsequence similarity, Landmarks similarity, angular metric for shape similarity (AMSS), and other linear programming and dynamic programming approaches among others. Dimensionality reduction techniques such as piecewise aggregate approximation and others may also be employed as a processing step in shape similarity comparisons for shape matching.

Another embodiment classifies one or more subsurface properties in a geographic region without calibration. Herein, the sensing tool is deployed at a location that does not have a predefined representative reference soil series. Responsive to obtaining depth varying measurements from the sensing tool, said signals are corresponded to a classification chart such as a soil texture triangle, Munsell color chart etc., and determined properties from the chart are used to compute an actual reference soil series for the location.

The manner of classifying one or more subsurface properties in a geographic region is unavailable in the presently available methods in the technological field of endeavor pertaining to soil surveying and mapping. A method of an embodiment described herein, when implemented to execute on a device or data processing system, comprises substantial advancement of the functionality of that device or data processing system in configuring depth varying measurements, then uses the measurements to generate signatures and models to classify a subject soil in a geographic region using soil property sensing tool. Raw measurements may also be used to classify subject soils directly.

The illustrative embodiments are described with respect to certain types of sensing tools 122 such as a penetrometer that includes one or more sensors 124 for measurement of soil attributes, comprising imaging sensors, pressure sensors, Global Positioning System (GPS), water content sensors, depth sensors, near-infrared reflectometry sensors, electrical conductivity or electrical resistivity sensors, electrical impedance spectroscopy sensors, acoustic sensors, etc. The penetrometer may also include one or more quasi-coaxial probes that are formed of a printed flex circuit. The one or more probes may comprise different layers of the printed circuit structure that are commonly coaxially aligned. They may also include energy harvesting and storage circuitry and components. In an illustrative embodiment, the penetrometer is a multi-sensor penetrometer probe and classifications described herein use values of soil properties obtained using the multi-sensor penetrometer probe and the geospatial location from which the values are obtained to determine which soil Series and Horizon within the NRCS (Natural Resources Conservation Service) registry ascribed to that geospatial location or to a proximate location (since NRCS boundaries are not exactly accurate) the probe measurements most represent. Thus, the soil in which the probe measurements were obtained is classified as the soil in the NRCS registry that is the nearest within the context of the soil property space. This enables refinement of the spatial fidelity of NRCS soil map s based on probe measurements, specifically with regard to layers present, layer thicknesses, and depths. Further the penetrometer may be configured to automatically measure soil properties and automatically carry out one or more, or even all steps described herein.

The illustrative embodiments are also described with respect to other scenes, subjects, measurements, devices, data processing systems, environments, components, and applications only as examples. Any specific manifestations of these and other similar artifacts are not intended to be limiting to the invention. Any suitable manifestation of these and other similar artifacts can be selected within the scope of the illustrative embodiments.

Furthermore, the illustrative embodiments may be implemented with respect to any type of data, data source, or access to a data source over a data network. Any type of data storage device may provide the data to an embodiment of the invention, either locally at a data processing system or over a data network, within the scope of the invention. Where an embodiment is described using a mobile device, any type of data storage device suitable for use with the mobile device may provide the data to such embodiment, either locally at the mobile device or over a data network, within the scope of the illustrative embodiments.

The illustrative embodiments are described using specific surveys, code, hardware, algorithms, designs, architectures, protocols, layouts, schematics, and tools only as examples and are not limiting to the illustrative embodiments. Furthermore, the illustrative embodiments are described in some instances using particular software, tools, and data processing environments only as an example for the clarity of the description. The illustrative embodiments may be used in conjunction with other comparable or similarly purposed structures, systems, applications, or architectures. For example, other comparable mobile devices, structures, systems, applications, or architectures therefor, may be used in conjunction with such embodiment of the invention within the scope of the invention. An illustrative embodiment may be implemented in hardware, software, or a combination thereof.

The examples in this disclosure are used only for the clarity of the description and are not limiting to the illustrative embodiments. Additional data, operations, actions, tasks, activities, and manipulations will be conceivable from this disclosure and the same are contemplated within the scope of the illustrative embodiments.

Any advantages listed herein are only examples and are not intended to be limiting to the illustrative embodiments. Additional or different advantages may be realized by specific illustrative embodiments. Furthermore, a particular illustrative embodiment may have some, all, or none of the advantages listed above.

Figure 2:
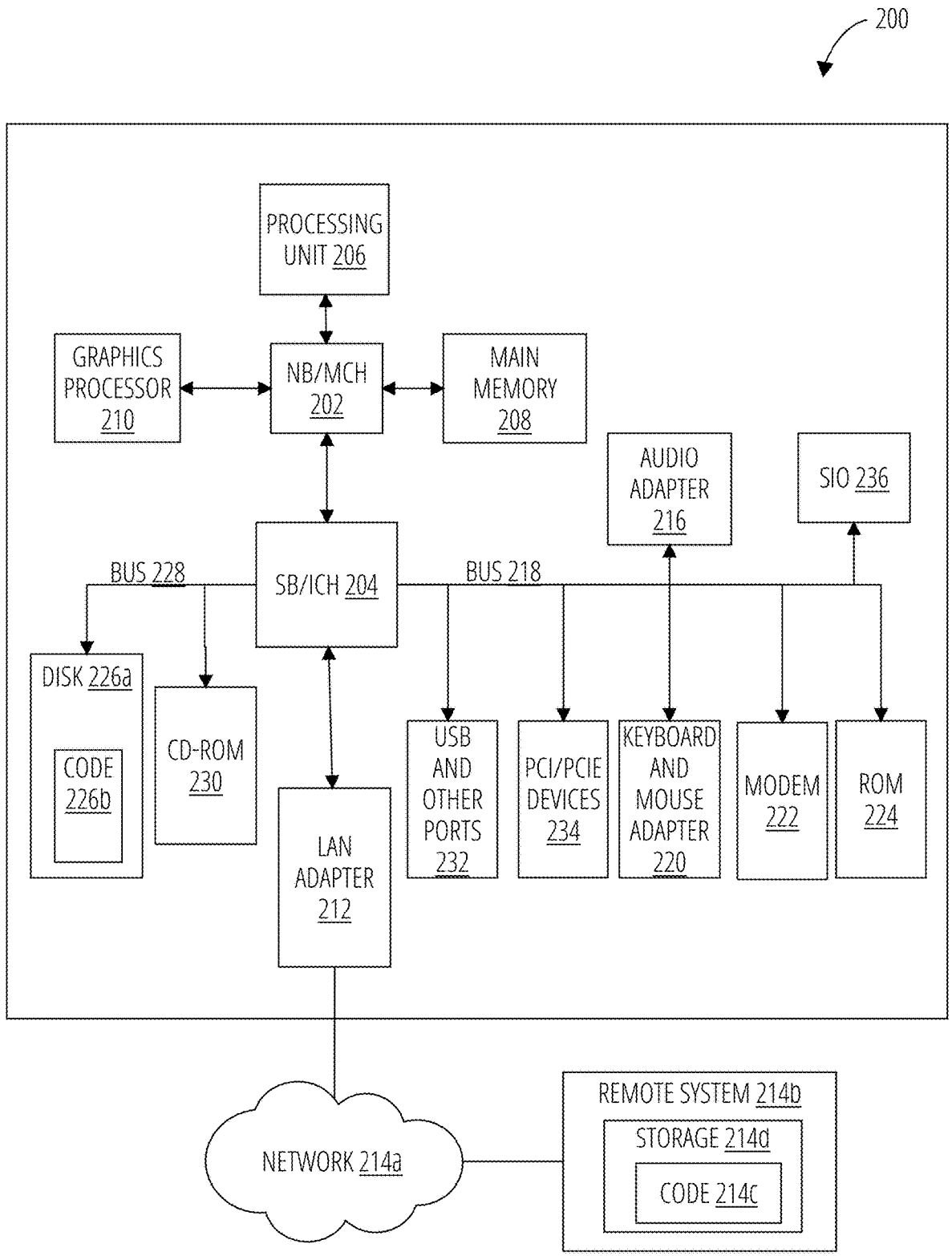
FIG. 2 depicts a block diagram of a data processing system in which illustrative embodiments may be implemented.

With reference to the figures and in particular with reference to FIG. 1 and FIG. 2, these figures are example diagrams of data processing environments in which illustrative embodiments may be implemented. FIG. 1 and FIG. 2 are only examples and are not intended to assert or imply any limitation with regard to the environments in which different embodiments may be implemented. A particular implementation may make many modifications to the depicted environments based on the following description.

FIG. 1 depicts a block diagram of a network of data processing systems in which illustrative embodiments may be implemented. Data processing environment 100 is a network of computers in which the illustrative embodiments may be implemented. Data processing environment 100 includes network 102. Network 102 is the medium used to provide communications links between various devices and computers connected together within data processing environment 100. Network 102 may include connections, such as wire, wireless communication links, or fiber optic cables.

Clients or servers are only example roles of certain data processing systems connected to network 102 and are not intended to exclude other configurations or roles for these data processing systems. Server 104 and server 106 couple to network 102 along with storage unit 108. Software applications may execute on any computer in data processing environment 100. Client 110, client 112, client 114 are also coupled to network 102. A data processing system, such as server 104 or server 106, or clients (client 110, client 112, client 114) may contain data and may have software applications or software tools executing thereon.

Only as an example, and without implying any limitation to such architecture, FIG. 1 depicts certain components that are usable in an example implementation of an embodiment. For example, servers and clients are only examples and not to imply a limitation to a client-server architecture. As another example, an embodiment can be distributed across several data processing systems and a data network as shown, whereas another embodiment can be implemented on a single data processing system within the scope of the illustrative embodiments. Data processing systems (server 104, server 106, client 110, client 112, client 114) also represent example nodes in a cluster, partitions, and other configurations suitable for implementing an embodiment.

Device 120 is an example of a device described herein. For example, device 120 can take the form of a smartphone, a tablet computer, a laptop computer, client 110 in a stationary or a portable form, a wearable computing device, or any other suitable device. Any software application described as executing in another data processing system in FIG. 1 can be configured to execute in device 120 in a similar manner. Any data or information stored or produced in another data processing system in FIG. 1 can be configured to be stored or produced in device 120 in a similar manner.

Sensing tool 122 includes one or more sensors 124 that measure depth varying attributes of a soil when deployed at a geographical location. The sensing tool 122 measures values of the one or more subsurface properties at a first location within the geographic region. An example sensing tool 122 is a penetrometer configured to continuously measure a plurality of soil attributes as the penetrometer is being inserted in a soil. Data generated by sensing tool 122 can be stored in database 118 of storage unit 108. Database 118 also stores one or more soil reference profiles and classification charts in repositories for computations herein.

Application 116 implements an embodiment described herein. Application 116 can use data from sensing tool 122 to characterize soil. Application 116 can also obtain data from storage unit 108 to characterize soil. Application 116 can also execute in any of data processing systems (server 104 or server 106, client 110, client 112, client 114), such as client application 126 in client 110 and need not execute in the same system as server 104.

Server 104, server 106, storage unit 108, client 110, client 112, client 114, device 120 may couple to network 102 using wired connections, wireless communication protocols, or other suitable data connectivity. Client 110, client 112 and client 114 may be, for example, personal computers or network computers.

In the depicted example, server 104 may provide data, such as boot files, operating system images, and applications to client 110, client 112, and client 114. Client 110, client 112 and client 114 may be clients to server 104 in this example. Client 110, client 112 and client 114 or some combination thereof, may include their own data, boot files, operating system images, and applications. Data processing environment 100 may include additional servers, clients, and other devices that are not shown. Server 104 includes an application 116 that may be configured to implement one or more of the functions described herein for soil characterization using identified soil attribute to reference soil series dependency relationships in accordance with one or more embodiments.

Server 106 includes a search engine configured to search classification charts, reference soil series, and stored sensor data images from one or more repositories in response to a query as described herein with respect to various embodiments.

In the depicted example, data processing environment 100 may be the Internet. Network 102 may represent a collection of networks and gateways that use the Transmission Control Protocol/Internet Protocol (TCP/IP) and other protocols to communicate with one another. At the heart of the Internet is a backbone of data communication links between major nodes or host computers, including thousands of commercial, governmental, educational, and other computer systems that route data and messages. Of course, data processing environment 100 also may be implemented as a number of different types of networks, such as for example, an intranet, a local area network (LAN), or a wide area network (WAN). FIG. 1 is intended as an example, and not as an architectural limitation for the different illustrative embodiments.

Among other uses, data processing environment 100 may be used for implementing a client-server environment in which the illustrative embodiments may be implemented. A client-server environment enables software applications and data to be distributed across a network such that an application functions by using the interactivity between a client data processing system and a server data processing system. Data processing environment 100 may also employ a service-oriented architecture where interoperable software components distributed across a network may be packaged together as coherent business applications. Data processing environment 100 may also take the form of a cloud, and employ a cloud computing model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service.

With reference to FIG. 2, this figure depicts a block diagram of a data processing system in which illustrative embodiments may be implemented. Data processing system 200 is an example of a computer, such as server 104, server 106, or client 110, client 112, client 114 in FIG. 1, or another type of device in which computer usable program code or instructions implementing the processes may be located for the illustrative embodiments.

Data processing system 200 is also representative of a data processing system or a configuration therein, such as device 120 in FIG. 1 in which computer usable program code or instructions implementing the processes of the illustrative embodiments may be located. Data processing system 200 is described as a computer only as an example, without being limited thereto. Implementations in the form of other devices, such as device 120 in FIG. 1, may modify data processing system 200, such as by adding a touch interface, and even eliminate certain depicted components from data processing system 200 without departing from the general description of the operations and functions of data processing system 200 described herein.

In the depicted example, data processing system 200 employs a hub architecture including North Bridge and memory controller hub (NB/MCH) 202 and South Bridge and input/output (I/O) controller hub (SB/ICH) 204. Processing unit 206, main memory 208, and graphics processor 210 are coupled to North Bridge and memory controller hub (NB/MCH) 202. Processing unit 206 may contain one or more processors and may be implemented using one or more heterogeneous processor systems. Processing unit 206 may be a multi-core processor. Graphics processor 210 may be coupled to North Bridge and memory controller hub (NB/MCH) 202 through an accelerated graphics port (AGP) in certain implementations.

In the depicted example, local area network (LAN) adapter 212 is coupled to South Bridge and input/output (I/O) controller hub (SB/ICH) 204. Audio adapter 216, keyboard and mouse adapter 220, modem 222, read only memory (ROM) 224, universal serial bus (USB) and other ports 232, and PCI/PCIe devices 234 are coupled to South Bridge and input/output (I/O) controller hub (SB/ICH) 204 through bus 218. Hard disk drive (HDD) or solid-state drive (SSD) 226a and CD-ROM 230 are coupled to South Bridge and input/output (I/O) controller hub (SB/ICH) 204 through bus 228. PCI/PCIe devices 234 may include, for example, Ethernet adapters, add-in cards, and PC cards for notebook computers. PCI uses a card bus controller, while PCIe does not. Read only memory (ROM) 224 may be, for example, a flash binary input/output system (BIOS). Hard disk drive (HDD) or solid-state drive (SSD) 226a and CD-ROM 230 may use, for example, an integrated drive electronics (IDE), serial advanced technology attachment (SATA) interface, or variants such as external-SATA (eSATA) and micro-SATA (mSATA). A super I/O (SIO) device 236 may be coupled to South Bridge and input/output (I/O) controller hub (SB/ICH) 204 through bus 218.

Memories, such as main memory 208, read only memory (ROM) 224, or flash memory (not shown), are some examples of computer usable storage devices. Hard disk drive (HDD) or solid-state drive (SSD) 226a, CD-ROM 230, and other similarly usable devices are some examples of computer usable storage devices including a computer usable storage medium.

An operating system runs on processing unit 206. The operating system coordinates and provides control of various components within data processing system 200 in FIG. 2. The operating system may be a commercially available operating system for any type of computing platform, including but not limited to server systems, personal computers, and mobile devices. An object-oriented or other type of programming system may operate in conjunction with the operating system and provide calls to the operating system from programs or applications executing on data processing system 200.

Instructions for the operating system, the programming system, and applications or programs, such as application 116 and client application 126 in FIG. 1, are located on storage devices, such as in the form of codes 226b on Hard disk drive (HDD) or solid-state drive (SSD) 226a, and may be loaded into at least one of one or more memories, such as main memory 208, for execution by processing unit 206. The processes of the illustrative embodiments may be performed by processing unit 206 using computer implemented instructions, which may be located in a memory, such as, for example, main memory 208, read only memory (ROM) 224, or in one or more peripheral devices.

Furthermore, in one case, code 226b may be downloaded over network 214a from remote system 214b, where similar code 214c is stored on a storage device 214d in another case, code 226b may be downloaded over network 214a to remote system 214b, where downloaded code 214c is stored on a storage device 214d.

The hardware in FIG. 1 and FIG. 2 may vary depending on the implementation. Other internal hardware or peripheral devices, such as flash memory, equivalent non-volatile memory, or optical disk drives and the like, may be used in addition to or in place of the hardware depicted in FIG. 1 and FIG. 2. In addition, the processes of the illustrative embodiments may be applied to a multiprocessor data processing system.

In some illustrative examples, data processing system 200 may be a personal digital assistant (PDA), which is generally configured with flash memory to provide non-volatile memory for storing operating system files and/or user-generated data. A bus system may comprise one or more buses, such as a system bus, an I/O bus, and a PCI bus. Of course, the bus system may be implemented using any type of communications fabric or architecture that provides for a transfer of data between different components or devices attached to the fabric or architecture.

A communications unit may include one or more devices used to transmit and receive data, such as a modem or a network adapter. A memory may be, for example, main memory 208 or a cache, such as the cache found in North Bridge and memory controller hub (NB/MCH) 202. A processing unit may include one or more processors or CPUs.

The depicted examples in FIG. 1 and FIG. 2 and above-described examples are not meant to imply architectural limitations. For example, data processing system 200 also may be a tablet computer, laptop computer, or telephone device in addition to taking the form of a mobile or wearable device.

Where a computer or data processing system is described as a virtual machine, a virtual device, or a virtual component, the virtual machine, virtual device, or the virtual component operates in the manner of data processing system 200 using virtualized manifestation of some or all components depicted in data processing system 200. For example, in a virtual machine, virtual device, or virtual component, processing unit 206 is manifested as a virtualized instance of all or some number of hardware processing units 206 available in a host data processing system, main memory 208 is manifested as a virtualized instance of all or some portion of main memory 208 that may be available in the host data processing system, and Hard disk drive (HDD) or solid-state drive (SSD) 226a is manifested as a virtualized instance of all or some portion of Hard disk drive (HDD) or solid-state drive (SSD) 226a that may be available in the host data processing system. The host data processing system in such cases is represented by data processing system 200.

Figure 3:
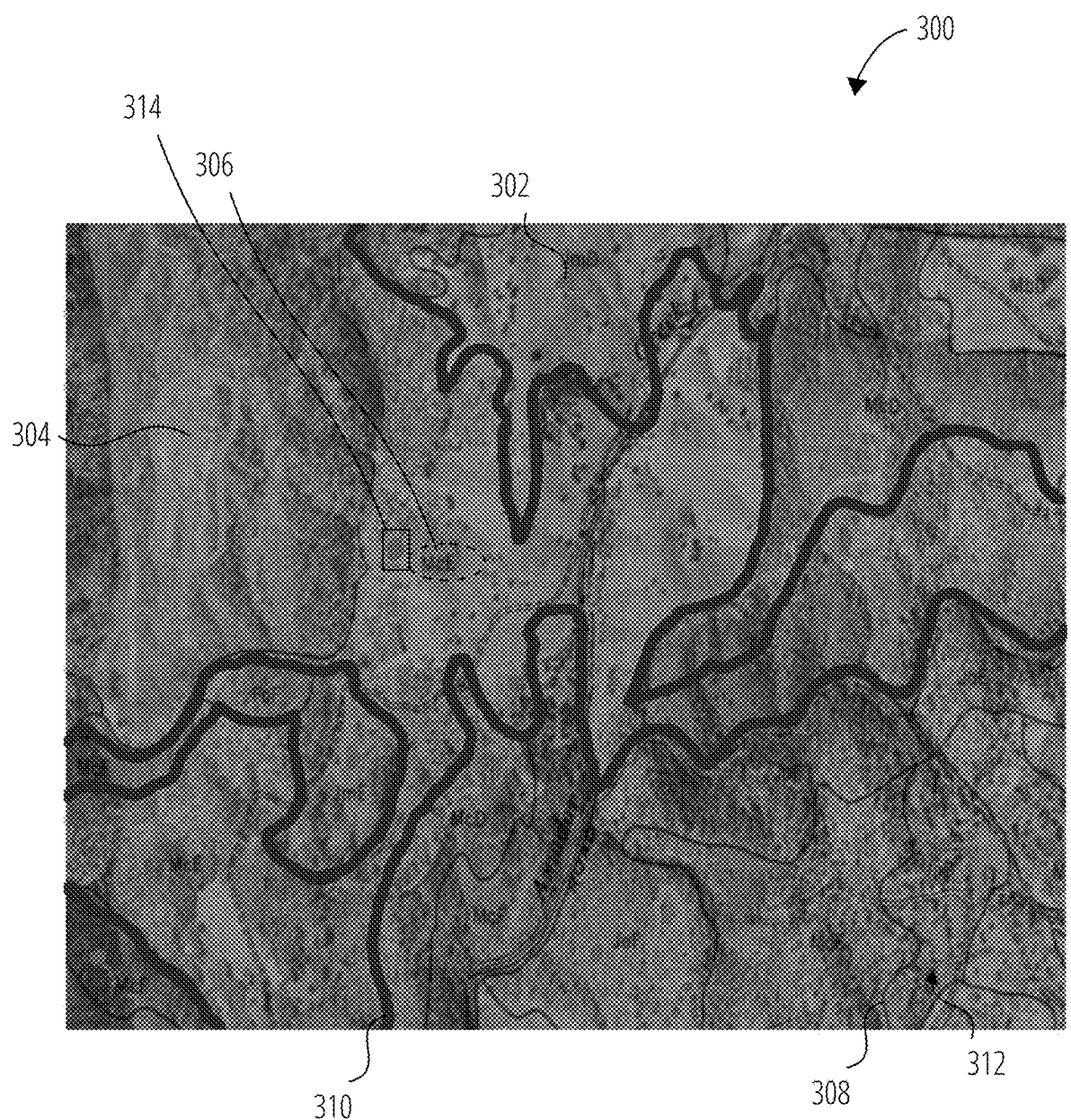
FIG. 3 depicts a sketch of a soil map in accordance with an illustrative embodiment.

FIG. 3 shows a soil map 300 having a plurality of soil map units 312 each with a closed boundary 308 and a label. An example label "McE" shows a soil map unit McE 306 shown with a thick boundary 310 for illustration herein. Other soil map units 312 shown in FIG. 3 include soil map units McD, JoE, JmD, JmE, for example.

A soil map unit 312 generally comprises one or more components. Each component represents polypedons that belong to a particular soil series, the name/label of the soil map unit usually being named after the soil series of the dominant component/polypedons within the unit. For example, the dominant component of an illustrative soil map unit LhE—Lily sandy loam, 15 to 35 percent slopes, very stony in the Greenbrier County, West Virginia soil survey (not shown) is classified as the Lily series, which comprises 80% of the soil map unit. The remaining 20% of the soil map unit consists of the Dekalb series, Berks series, and "soils that have stones covering less of the surface" than the Lily series.

Some of the characteristics commonly used to differentiate series are the kind, thickness, and arrangement of horizons and their structure, color, redoximorphic features, texture, reaction, consistence, content of carbonates and other salts, content of humus, content of rock fragments, temperature, kinds and thickness of human-altered materials, and mineralogical composition. In an illustrative embodiment, the sensing tool 122 is configured to measure said characteristics continuously with increasing depth of soil at a deployed location. A significant difference in any one of said characteristics may be the basis for recognizing a different series. Though rare, two soil series may differ in just one of these characteristics. Most characteristics are related, and generally several change together. Said characteristics are generally referred to herein as subsurface properties.

Knowing one or more soil series of a piece of land allows a plethora of predetermined information affiliated with the one or more soil series to be fetched and used in analysis and decision making pertinent to that location. For example, interpretive features such as ecological site descriptions can be obtained from the descriptions and characterization of soils for optimal use of the land.

In an illustrative embodiment, soil map 300 comprises a plurality of first locations 302 and one or more second locations 304. Each of the plurality of first locations 302 belongs to a soil map unit 312 and is a location or coordinate that is manually recorded by an operator such as a soil scientist by generating a pedon or digging a pit in the soil at that location. Soil scientists manually record the characteristics of the pit created at the plurality of first locations 302, associated plant communities, geology, landforms, etc. The kind and arrangement of soil horizons and their color, texture, size and shape of soil aggregates, or otherwise subsurface properties are observed to classify and identify soils in the plurality of first locations 302. After the soil scientists identify and describe the properties of landscape components, or natural bodies of soils, the components are correlated to an appropriate taxonomic class, which is used to generate the labels for naming the soil map unit 312. This provides "ground truth" information, that can be utilized for developmental purposes. Said ground truth information has been predetermined for the plurality of first locations 302, in the illustrative embodiment. In the illustrative embodiment, the plurality of manually recorded first locations 302 are used in a subsequent digital calibration step. Herein, a sensing tool 122 configured to obtain a continuous measurement of the subsurface properties is deployed at each of the plurality of first locations 302. The outputs of the sensing tool 122 are used as or normalized into digital signature models for each of said plurality of first locations 302, with said digital signature models being corresponded to the predetermined reference soil series of its respective first location 302.

In an illustrative example, predefined reference soils series Mariposa Series is the dominant component of soil map unit McE 306—Mariposa very rocky loam, 31 to 51 percent slope. The boundary for soil map unit McE 306, shown as a thick boundary 310 for illustration purposes, covers a much larger area than an area cover by soil map unit JmD to the north of soil map unit McE 306. Assuming that only one pit was used in the mapping of soil map unit McE 306 at, for example at pit location L-McE 314, then second location 304 may be different from the Mariposa Series and therefore have a unit name that is different from Mariposa very rocky loam, 31 to 51 percent slope. Thus, the inherited classification determined by virtue of its placement within thick boundary 310 may be incorrect.

By profiling each of the plurality of first locations 302 in soil map 300 using a standardized sensing tool 122 in order to obtain and stored standardized digital models or signatures corresponding to their predetermined reference soil series or map units, unmapped, wrongly mapped or minimally mapped locations, referred to herein as second locations 304, can be subsequently profiled and their digital signatures compared to the stored standardized signatures for "actual" classification. Therefore, deploying sensing tool 122 at said second location 304 and determining signatures for corresponding subsurface properties of the second location 304, enables an actual reference soil series or mapping unit to be determined. Repeating the process for a plurality of other second locations 304 as described herein significantly increases the spatial resolution of a soil map 300 and allows optimal use of land in the soil map 300.

Figure 4A:
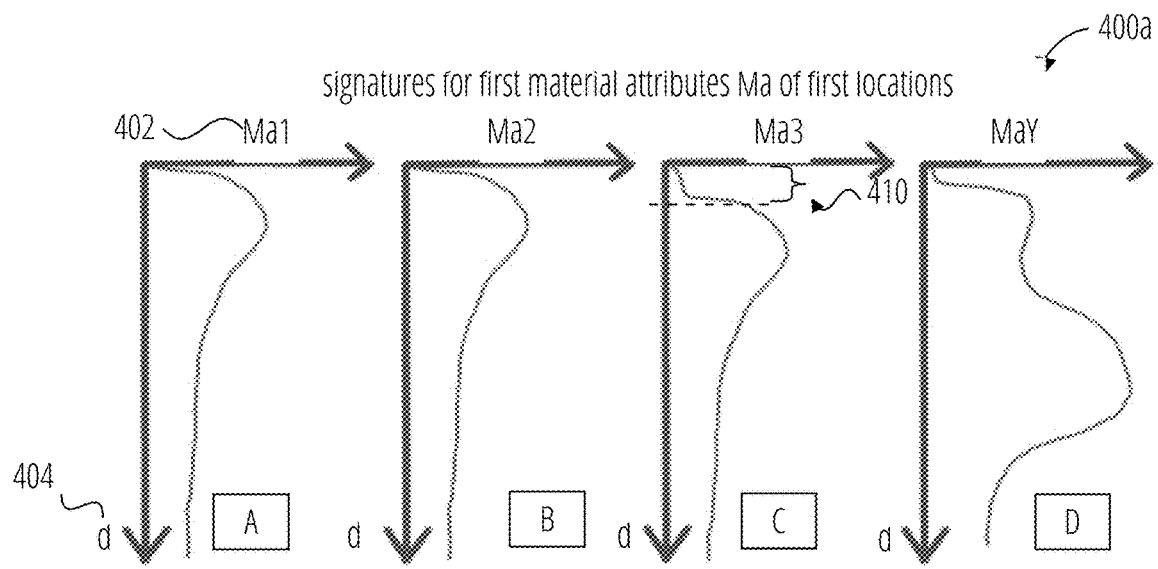
FIG. 4A depicts a chart showing signatures for first properties of first locations according to an illustrative embodiment.

FIG. 4A shows charts 400a of signatures for first subsurface properties Ma of a plurality of first locations 302 that each have a predefined reference soil series. In the embodiment, the first locations 302 include locations 1-Y and the first subsurface properties include Ma1-MaY. The charts show variations of subsurface properties 402 with increasing depth 404 of soil at said locations. In an exemplary embodiment, Ma is a texture property of the soil at said locations. The signatures are determined by deploying the sensing tool 122 at said locations and measuring the variation in the properties at the locations.

Figure 4B:
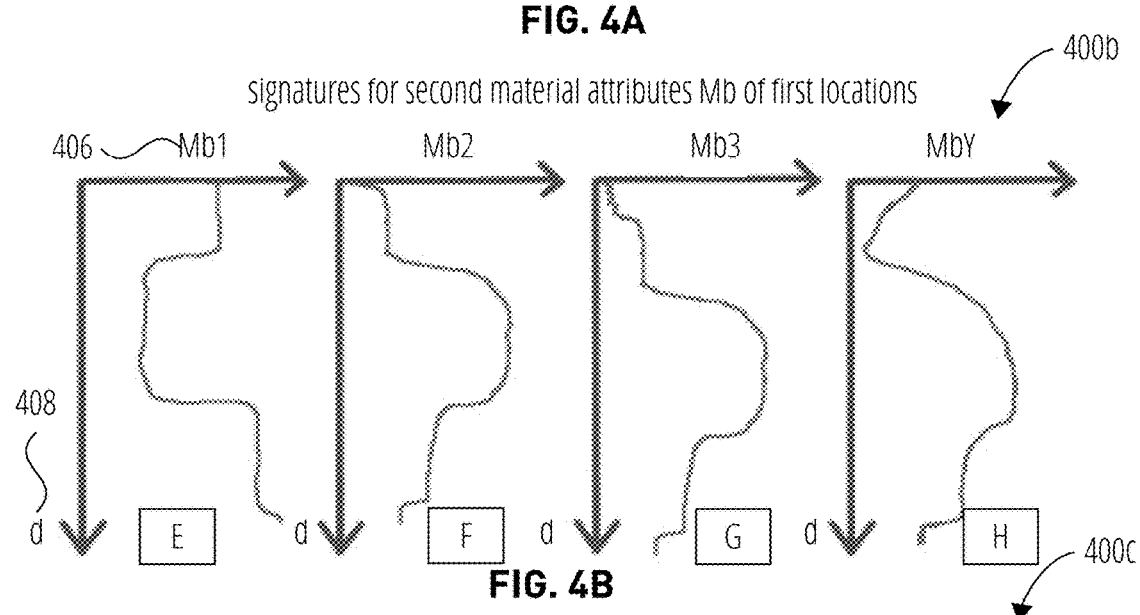
FIG. 4B depicts a chart showing signatures for second properties of first locations according to an illustrative embodiment.

In the embodiment, FIG. 4B illustrates charts 400b of signatures for second properties Mb of said first locations 302 (locations 1-Y). The second subsurface properties include Mb1-MbY. The charts show variations of subsurface properties 406 with increasing depth 408 of soil at said locations. In an exemplary embodiment, Mb is a color attribute of the soil at said locations. The signatures are determined by deploying the sensing tool 122 at said first locations 302 and measuring the variation in the properties at the locations. In an example, property Ma1 for first location 1 and property Mb1 for first location 1 are measured concurrently when the sensing tool 122 is deployed at location 1. Sensing tool 122 is thus configured to measure a plurality of properties. Off course the examples in this disclosure are used only for the clarity of the description and are not limiting to the illustrative embodiments. Additional operations, actions, tasks, activities, and manipulations will be conceivable from this disclosure and the same are contemplated within the scope of the illustrative embodiments.

Once the properties are measured for first locations 302 (locations 1-Y), application 116 receives the measurements through network 102 for storage in database 118. In an illustrative embodiment, the measurements are normalized for storage. In another illustrative embodiment, the measurements are stored in raw form. Consequently, measurements are available for all depths of the soil through the depth varying continuous signatures. Moreover, data preparation steps can be applied to the measurements such as to remove extraneous values and outliers, fill in missing values, conform to a standardized pattern, generate representative models and the like. Any specific manifestations of these and other data preparations steps are not intended to be limiting to the invention.

Turning back to FIG. 4A, signatures A-D of a subsurface property Ma of locations 1-Y will now be compared. Signature A appears to be the same as or substantially similar to signature B whereas signature C is a vertically shifted 410 form of signature A or B. The shift may represent a new layer of soil at location 3 that is absent from locations 1 or 2. Signature D for location Y on the other hand differs significantly from any of the preceding signatures. In FIG. 4B, signature E and H are significantly different from any of the other signatures and signature G is a vertically shifted form of signature F.

In an illustrative embodiment, all signatures of a set of properties for a location are accumulated to form a combined model signature for storage or may be stored as individual signatures. Application 116 corresponds the stored signatures to predefined reference soil series or other taxonomies or soil map unit 312 in the database 118.

Figure 4C:
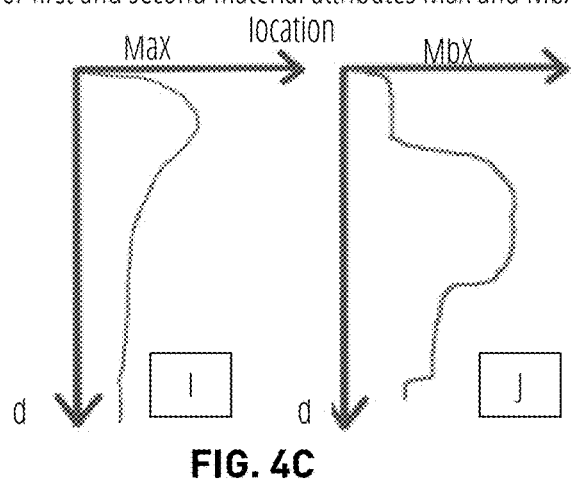
FIG. 4C depicts a chart showing signatures for first and second properties of a second location in accordance with an illustrative embodiment.
Figure 5:
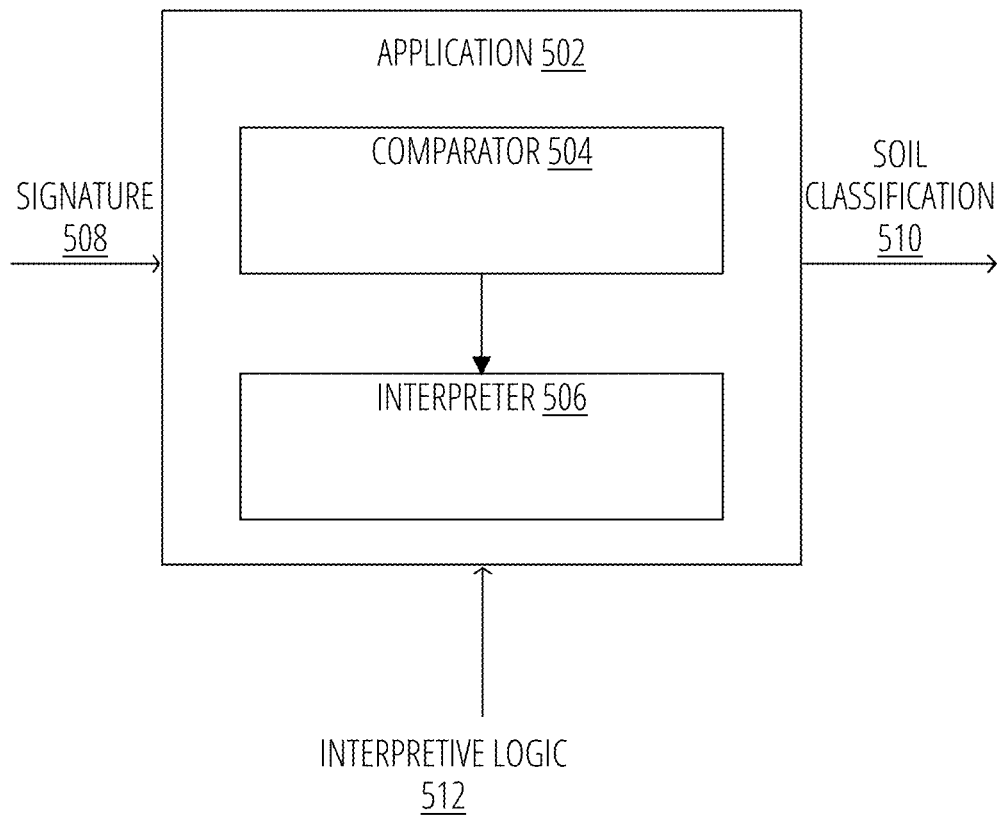
FIG. 5 depicts a block diagram of an illustrative application in accordance with one embodiment.

FIG. 4C illustrates signatures for first and second properties MaX and MbX of second location 304 (location X). In this case, the second location 304 is unmapped, minimally mapped or incorrectly mapped. Application 502 is used in a classification process herein. Application 502 is an example of Application 116 or client application 126. Application 502 determines from a comparator 504 that while signature I of subsurface property Ma (e.g. texture) for second location X is the same or substantially similar to signatures A and B of the same subsurface property Ma of first locations 1 and 2 respectively, signature J of subsurface property Mb (e.g. color) for second location X is only the same as or substantially similar (e.g. exceeds a threshold match of 90%) to signature F of subsurface property Mb of location 2 and not location 1. Thus application 116 determines from an interpreter 506 that takes the comparison as input that second location X has soil that belongs to the same series as the predefined reference soil series of first location 2.

The comparator 504 may be configured with any number of comparison techniques (such as descriptive or inferential statistics, cross-correlation, AI/ML (Artificial intelligence/Machine Learning) techniques, curve matching algorithms such as dynamic time warping (DTW), Euclidean distance between stratigraphic segmentations, and or quantum computing techniques for signature matching. In an example, a curve matching algorithm takes newly generated signatures as input and determines a closest matching previously stored reference signature. For example, the comparator determines that for a newly generated signature, a closest matching signature matches the newly generated signature by a maximum of 90% or by a maximum of 65%. Each reference signature obtained by deploying a sensing tool at a location is a digital twin or virtual replica of the location or properties of the location that can be used by data scientists to run simulations. In an exemplary embodiment herein, Application 502 aggregates output from the comparator. For example, the Application 502 aggregates matched signatures to obtain a soil property. The Application 502 may also aggregate soil properties to obtain a soil classification. In a further example, Application 502, the aggregates soil properties to obtain a soil site characterization. Thus, any combinations of the signatures, soil properties, soil classifications and soil site characterizations may be used to create additional digital twins for running simulations on soils. In another exemplary embodiment, that uses a machine learning technique, a neural network model is trained with a dataset of training signatures to yield desired outputs. This training dataset includes inputs signatures and correct output signatures, which allow the neural network model to learn over time. The algorithm measures its accuracy through a loss function, adjusting until the error has been sufficiently minimized. In another exemplary embodiment, a quantum computer is used. It may be used for example, to perform faster or optimized comparison of signatures. By exploiting quantum parallelism of qubits, in combination with data processing by a classical computer, associations between signatures can be easily identified for further use.

Interpreter 506 may be configured with any number of interpretive logic 512 that takes an output of the comparator as input and determines an actual series or classification for the newly generated signature. For example, the interpreter determines that based on defined interpretive logic 512, a 90% match satisfies a minimum threshold for determining an actual series. It therefore uses the predefined reference soil series of the matching signature or a related series thereof as the actual series of the new location.

Figure 6A:
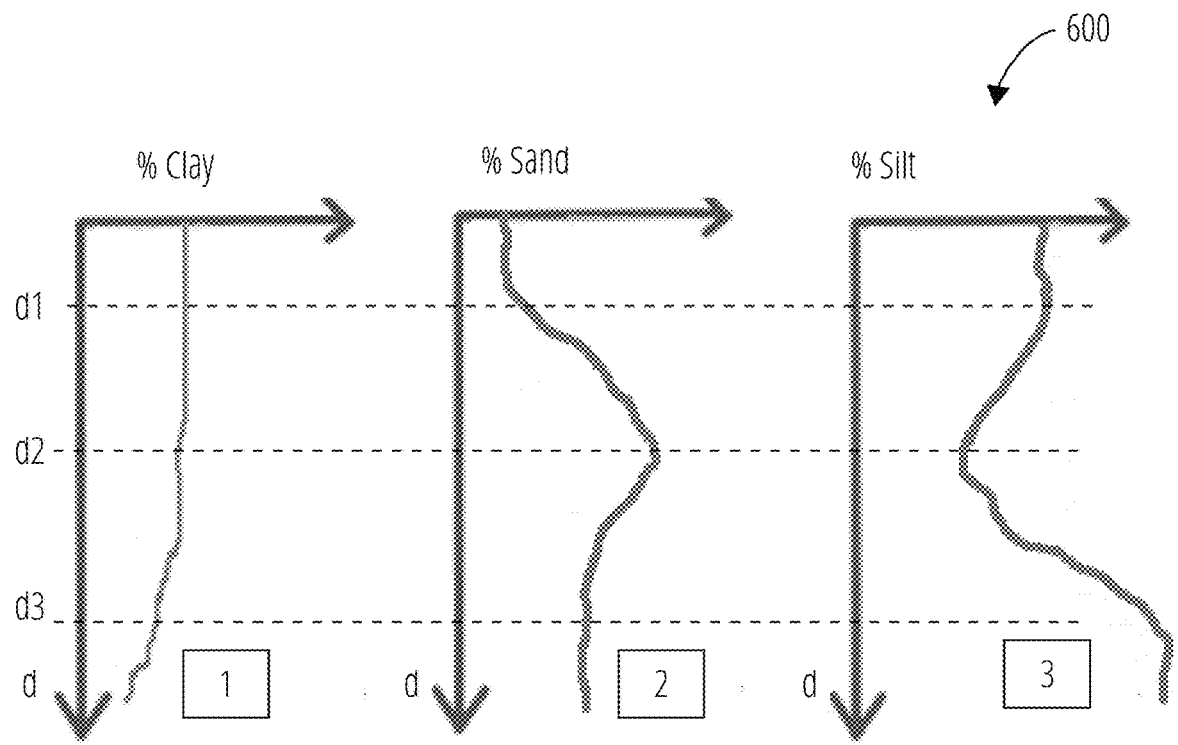
FIG. 6A depicts a chart showing texture signatures in accordance with an illustrative embodiment.

FIG. 6A shows another illustrative embodiment. The embodiment shows texture signatures 600 for a subject location that is yet to be mapped, is loosely mapped or is incorrectly mapped. In this specific embodiment, calibration using the plurality of first locations 302 may not be needed. Texture signatures 600 (depicted as signatures 1, 2, and 3) correspond to percentages of clay sand and silt at said subject location respectively. At depth d1, a measured percentage of clay by sensing tool 122 is ~35%. A measured percentage of sand is ~10% and a measured percentage of silt is ~55%. The percentages measured at locations d1, d2 and d3 are shown in the table below.

| depth | % Clay | % Sand | % Silt |
|---|---|---|---|
| d1 | 35 | 10 | 55 |
| d2 | 25 | 50 | 25 |
| d3 | 10 | 25 | 65 |

Figure 7:
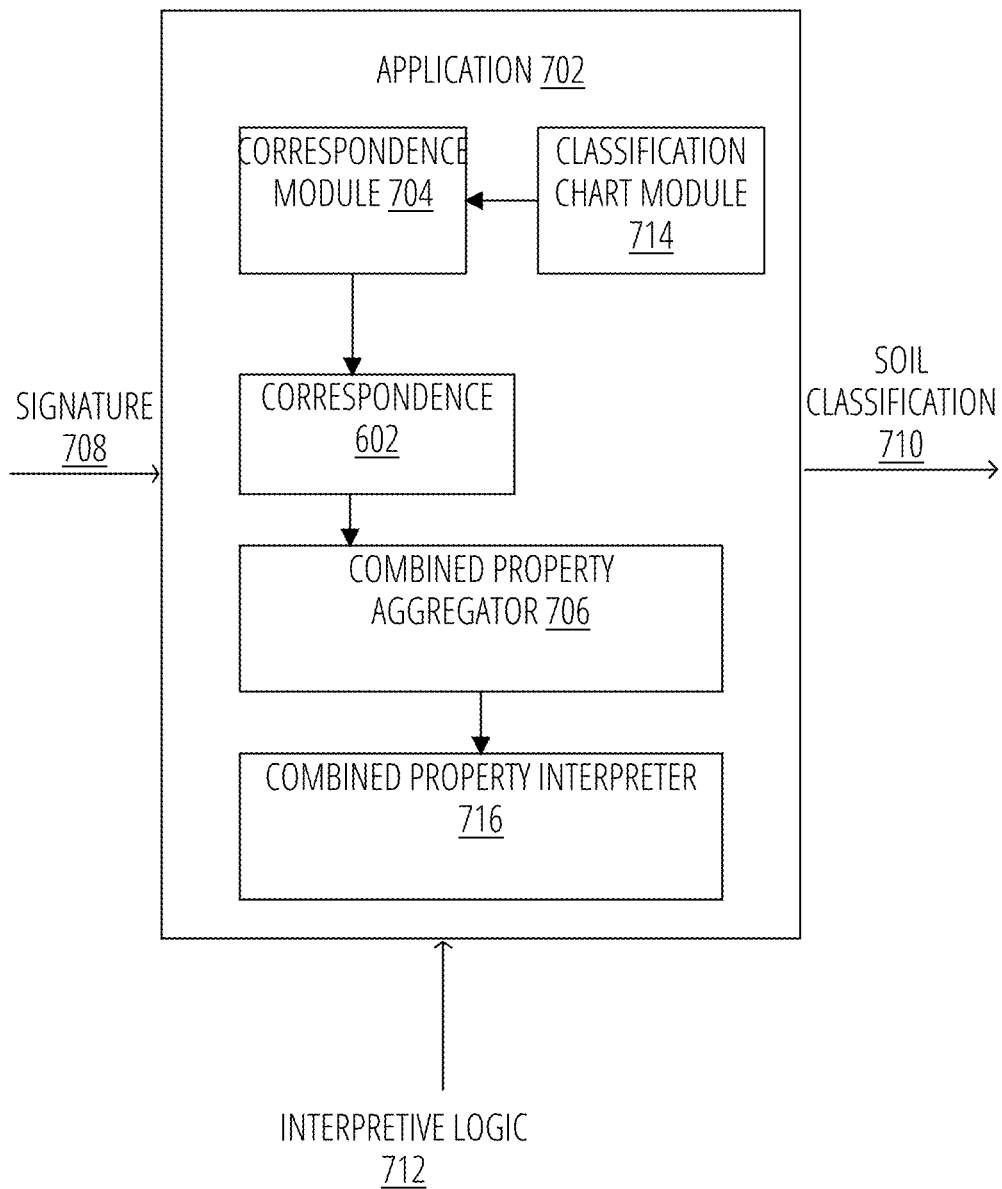
FIG. 7 depicts a block diagram of an illustrative application in accordance with one embodiment.

Application 702, shown in FIG. 7, receives signatures 1, 2 and 3. By using a soil texture triangle 604 obtained from a classification chart module 714, correspondence module 704 of application 702 corresponds the clay, sand and silt percentages to regions of the soil texture triangle 604 to obtain a continuous correspondence 602 of the texture attributes to property values on the soil texture triangle 604.

Figure 6B:
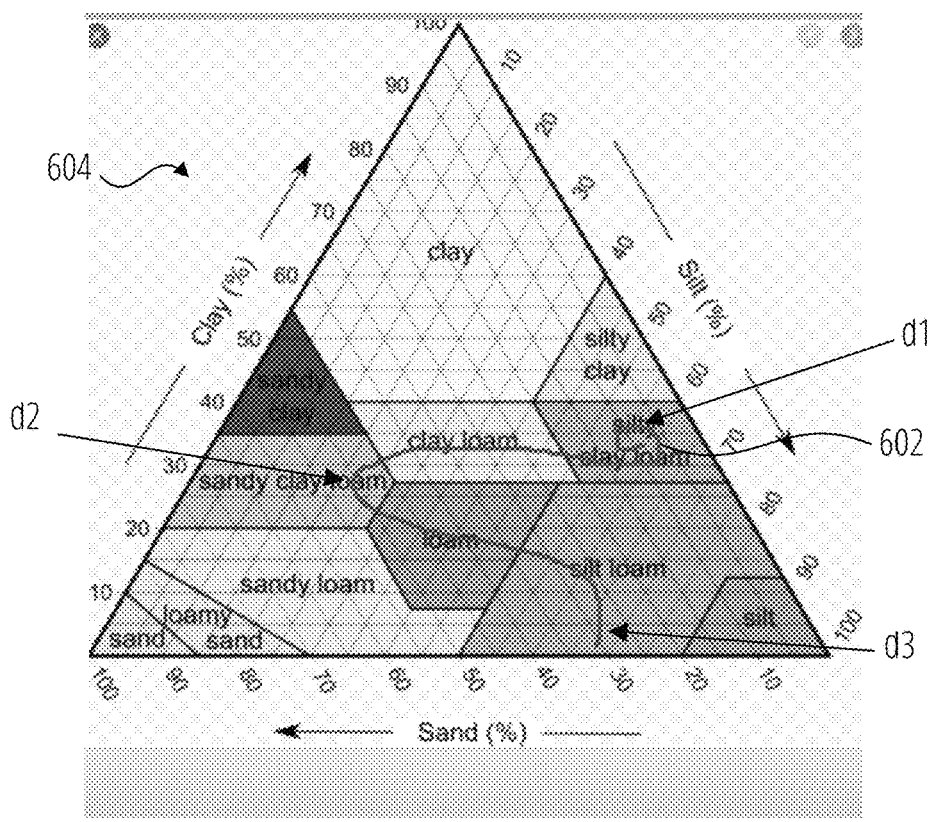
FIG. 6B depicts a chart of a soil texture triangle in accordance with one illustrative embodiment.

The correspondence 602 of FIG. 6B shows that at depth d1, the soil texture property at the subject location has a value of "silty clay loam" (35% Clay, 10% Sand, 55% Silt). At depth d2, the soil texture property at the subject location has a value of "sandy clay loam" (25% Clay, 50% Sand, 25% Silt), and at depth d3, the soil texture property at the subject location has a value of "silt loam" (10% Clay, 25% Sand, 65% Silt). Soil texture properties at other depths of the subject location, otherwise not readily discernible from the raw measurements of the sensing tool 122, are now obtainable from interpolation or extrapolation of the correspondence 602, the correspondence 602 generally being the matching of one or more measurements or signatures at a subject location to one or more soil property values of a classification chart such as a Munsell color chart or a soil texture triangle.

This is repeatable by application 702 for other signatures of other soil properties or subsurface properties (e.g. Soil structure, soil pH, soil color, soil carbon, soil water, etc.) using other corresponding classification charts. For example, measured colors obtained, for example, as raw output values from the sensing tool 122 deployed at the subject location, are corresponded to property values on a Munsell Color chart (not shown). A benefit herein is that values an optimal characterization of the soil color changes with increasing depth is possible.

Moreover, instead of correlating discrete values of the signatures to property values in the various classification charts, the signatures may be segmented into different clusters based on one or more segmentation algorithms. The segmentation may represent different horizons in a soil, for example. In a non-limiting example, an average of each cluster may be corresponded to values onto a classification chart to determine property values of the cluster. Of course, other methods of correlating signature values to available classification charts are possible in light of the description.

By corresponding a plurality of signatures of the subject location to one or more soil property values of a classification chart, standardized property descriptions are obtained. A combined property aggregator 706 is thus enabled to aggregate the standardized properties of the different subsurface properties of the subject location. A combined property interpreter 716 then determines a corresponding soil classification 710 or reference soil series for the subject location using the aggregated standardized property descriptions. This is based on, for example, a publicly available soil series description that matches the standardized property descriptions of the subject location.

Figure 8:
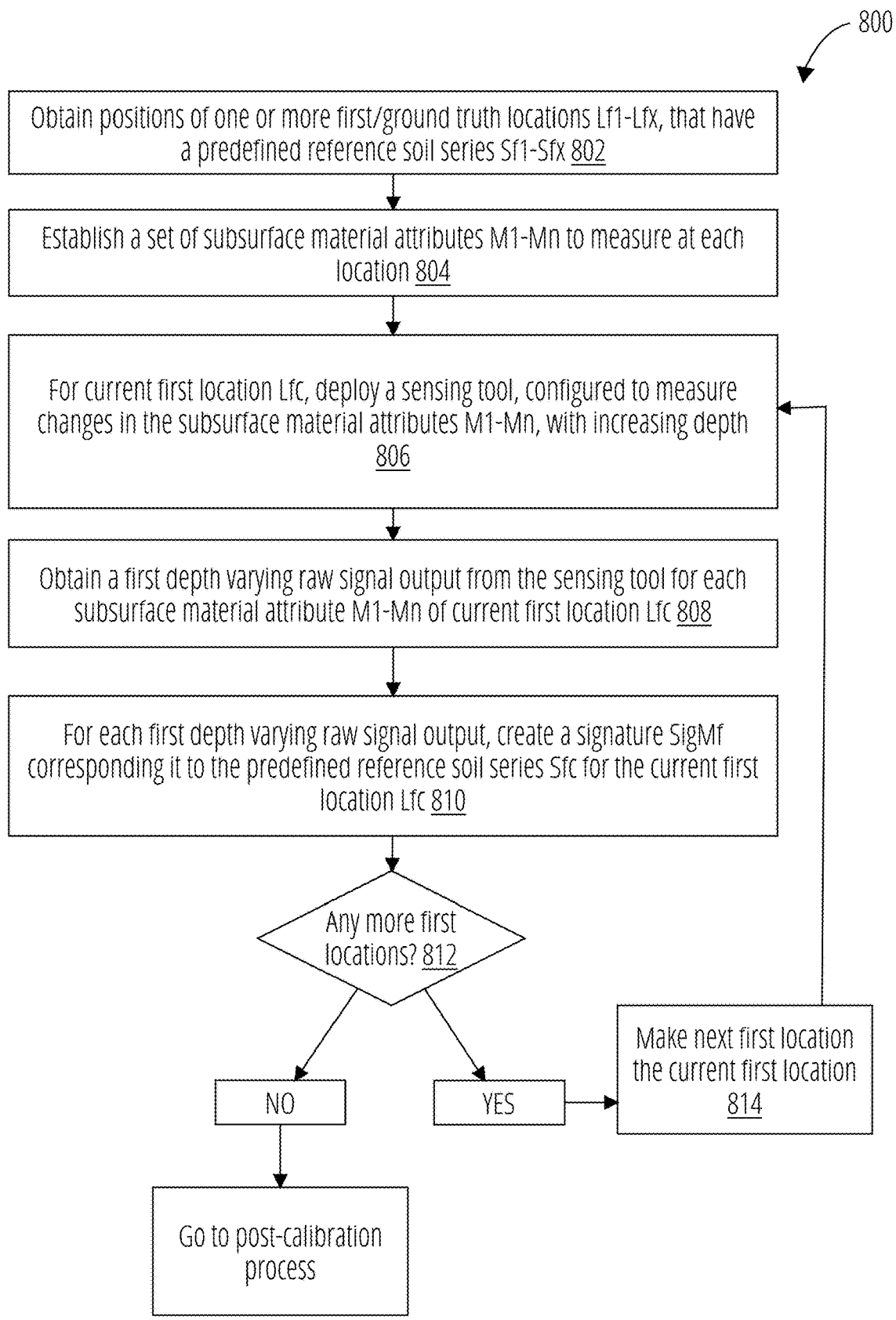
FIG. 8 depicts a calibration process according on an illustrative embodiment.

With reference to FIG. 8, the figure depicts a flowchart of a calibration process 800 according to an illustrative embodiment. Calibration is used herein to refer to a process of determining one or more signatures or measurements of one more subsurface properties for a first location 302 and corresponding the determined one or more signatures or measurements to a predefined reference soil series or classification of the first location 302.

In step 802, positions of one or more first/ground truth locations Lf1-Lfx are obtained. The locations have a predefined reference soil series Sf1-Sfx. In step 804, a set of subsurface properties M1-Mn needed for classification are established for measurement at each location. In step 806, a sensing tool is deployed at a current first location Lfc, the sensing tool 122 being configured to measure values of the subsurface properties M1-Mn, with increasing depth. In step 808, a first depth varying raw signal output is obtained from the sensing tool 122 for each subsurface property M1-Mn of current first location Lfc. In step 810, for each first depth varying raw signal output, a signature SigMf is created. This signature corresponds to the predefined reference soil series Sfc for the current first location Lfc. Moreover, a combined signature may be created using the individual signatures of the subsurface properties M1-Mn of current first location Lfc. In step 812, the calibration process 800 determines if any more first locations Lf1-Lfx remain to be profiled and repeats the deployment for the remaining locations (step 814). When all the locations are profiled, the post calibration process begins.

Figure 9:
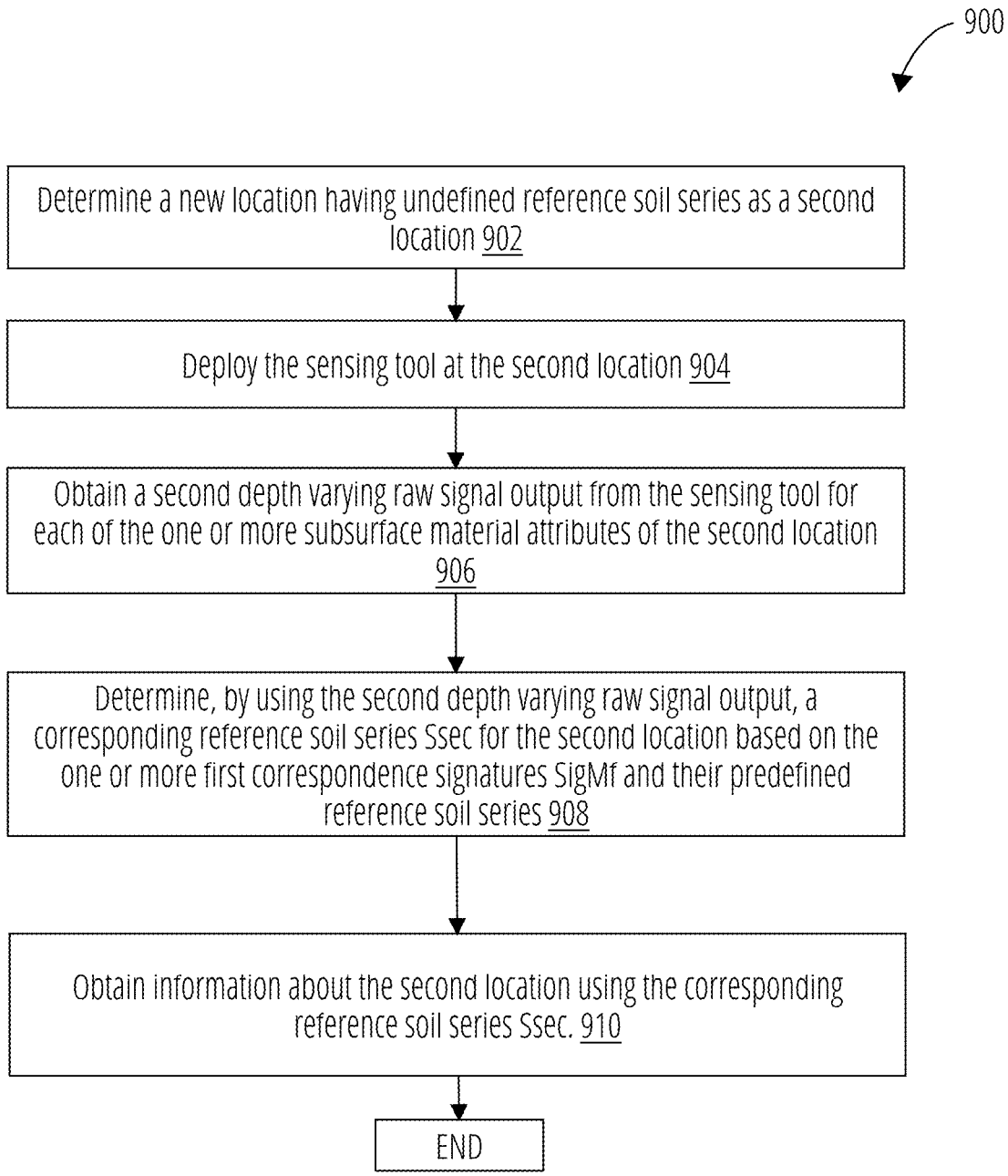
FIG. 9 depicts a post calibration process according on an illustrative embodiment.

With reference to FIG. 9, the figure is a flowchart illustrating a post calibration process 900 according to one embodiment. In step 902, the post calibration process 900 identifies a new location having undefined reference soil series as a second location. The new location can be, for example, a location that has undergone significant soil changes such as changes caused by flooding since it was first mapped. The new location can also be a location that is in the vicinity of a boundary 308 of an identified soil map unit 312 and this possibly incorrectly mapped. In step 904, the process deploys the sensing tool 122 at the second location. In step 906, the process obtains a second depth varying raw signal output from the sensing tool 122 for each of the one or more subsurface properties of the second location that are required for soil classification. In step 908, the process determines, by using the second depth varying raw signal output or a signature thereof, a corresponding reference soil series Ssec for the second location based on the one or more first signatures SigMf created in the calibration process 800 and their predefined reference soil series. In step 910, the post calibration process 900 obtains information about the second location using the corresponding reference soil series Ssec.

Figure 10:
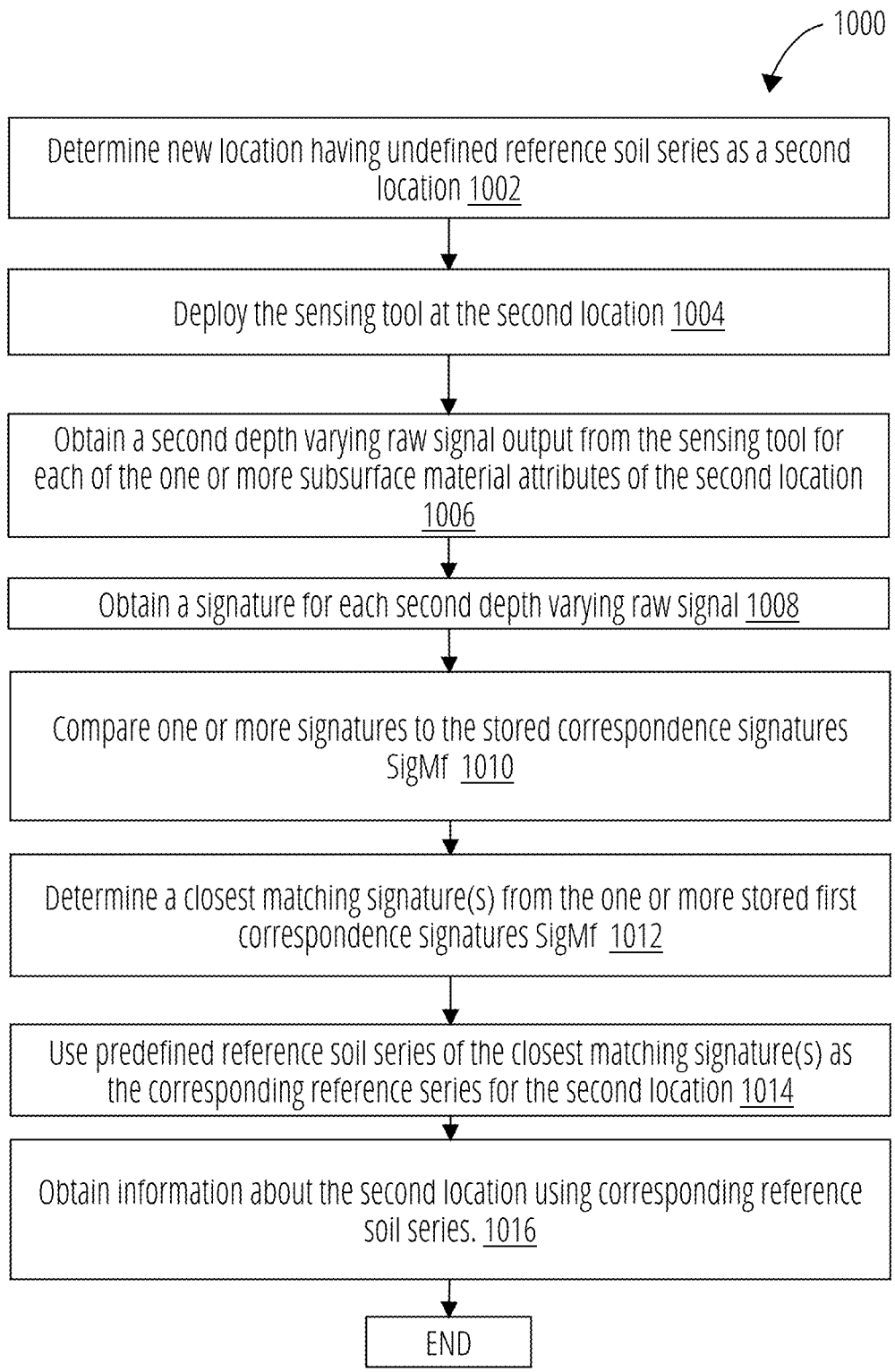
FIG. 10 depicts another post calibration process according on an illustrative embodiment.

With reference to FIG. 10, the figure depicts another post calibration process 1000 according to an illustrative embodiment. The process begins at step 1002, wherein a new location having an undefined or incorrect reference soil series is identified as a second location. In step 1004, the process deploys the sensing tool 122 at the second location. In step 1006, the process obtains from the sensing tool 122 a second depth varying raw signal output or signature for each of the one or more subsurface properties of the second location. In step 1008, the process obtains a signature for each second depth varying raw signal. In an embodiment, the signatures are the same as the depth varying raw signal output. In another embodiment, the signatures are different from the depth varying raw signal. In step 1010, the process compares one or more signatures to the stored correspondence signatures SigMf. The comparison can be achieved using curve matching techniques. Further discrete portions of the signatures can be used for comparison instead of a whole form of the signatures. Thus, in step 1012, the process determines a closest matching signature(s) from the one or more stored first correspondence signatures SigMf. In step 1014, the process uses a predefined reference soil series of the closest matching signature(s) or a variation thereof, based on a degree of similarity, as the corresponding reference series for the second location. In step 1016, the process obtains development and management information about the second location using corresponding reference soil series.

Figure 11:
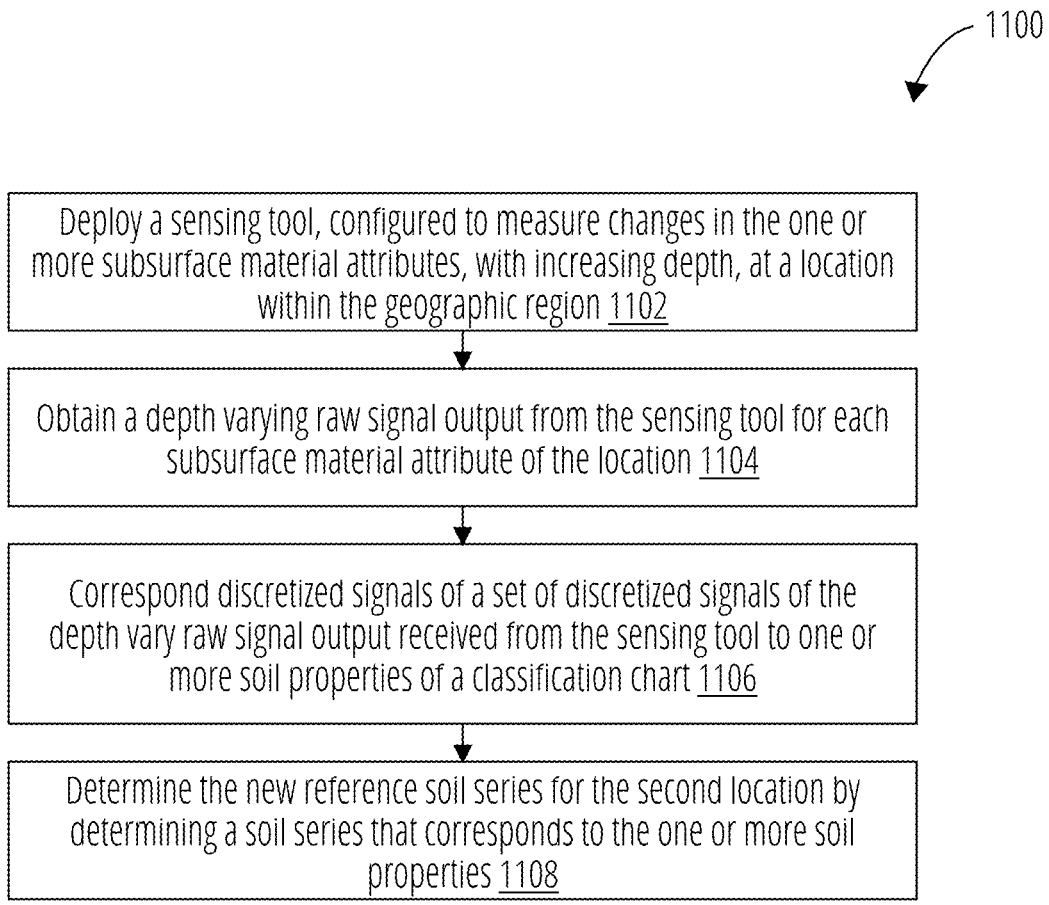
FIG. 11 depicts another classification process according to an illustrative embodiment.

With reference to FIG. 11, the figure depicts classification process 1100 according to an illustrative embodiment. The classification process 1100 determines properties of a soil at an unmapped, minimally mapped or incorrectly mapped location in a geographic region without a reliance on an earlier calibration step.

In step 1102, the process deploys a sensing tool 122, configured to measure values of the one or more subsurface properties, with increasing depth, at the location within the geographic region. In step 1104, the process obtains a depth varying raw signal output from the sensing tool for each subsurface property of the location. In step 1106, the process corresponds discretized signals of the depth varying raw signal output received from the sensing tool to one or more soil properties of a standardized classification chart. In step 1108, the process determines the new reference soil series for the location by determining a soil series that corresponds to the one or more soil properties obtained from the standardized classification chart.

Thus, a computer implemented method, system or apparatus, and computer program product are provided in the illustrative embodiments for soil classification and other related features, functions, or operations. Where an embodiment or a portion thereof is described with respect to a type of device, the computer implemented method, system or apparatus, the computer program product, or a portion thereof, are adapted or configured for use with a suitable and comparable manifestation of that type of device.

Where an embodiment is described as implemented in an application, the delivery of the application in a Software as a Service (SaaS) model is contemplated within the scope of the illustrative embodiments. In a SaaS model, the capability of the application implementing an embodiment is provided to a user by executing the application in a cloud infrastructure. The user can access the application using a variety of client devices through a thin client interface such as a web browser (e.g., web-based e-mail), or other light-weight client-applications. The user does not manage or control the underlying cloud infrastructure including the network, servers, operating systems, or the storage of the cloud infrastructure. In some cases, the user may not even manage or control the capabilities of the SaaS application. In some other cases, the SaaS implementation of the application may permit a possible exception of limited user-specific application configuration settings. Further, an Information as a Service (IaaS) is contemplated. A computing architecture and infrastructure in a virtual environment may be provided for a plurality of users wherein all computing resources such as data storage, virtualization, servers and networking may be accessed for use.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the sensing tool 122 or user's computer, partly on the user's computer or sensing tool 122, as a stand-alone software package, partly on the user's computer and partly on a remote computer or entirely on the remote computer or server, etc. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

All features disclosed in the specification, including the claims, abstract, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent, or similar purpose, unless expressly stated otherwise.

What is claimed is:

1. A method of characterizing soil properties of a subject soil located in an unmapped, wrongly mapped, or minimally mapped geographic location, wherein the subject soil does not have an associated or correct predefined and known soil classification, the method comprising:
deploying a sensing tool to a plurality of first geographic locations in differing classified soils that each have a corresponding predefined and known soil classification, wherein the sensing tool includes a plurality of sensors of differing types each configured to be responsive to one or more soil properties;
obtaining, at each of the plurality of first geographic locations, first depth varying raw signal outputs from the plurality of sensors at each of the plurality of first geographic locations;
creating for the first depth varying raw signal outputs from each of the plurality of first geographic locations, a corresponding first digital signature;
deploying the sensing tool to the subject soil at a second geographic location;
obtaining, at the second geographic location, second depth varying raw signal outputs from the plurality of sensors at the second geographic location;
creating for the second depth varying raw signal outputs from the second geographic location, a corresponding second digital signature;
comparing the second digital signature of the subject soil to the first digital signatures of the classified soils; and,
determining, based on the comparing and on the corresponding predefined and known soil classifications of the plurality of first geographic locations, a characterization of the subject soil at the second geographic location.

2. The method of claim 1, wherein the characterization of the subject soil comprises a first soil property.

3. The method of claim 1, wherein the characterization of the subject soil comprises a first soil classification.

4. The method of claim 1, wherein the characterization of the subject soil comprises a first soil site characterization.

5. The method of claim 1, wherein each predefined and known soil classification is a reference soil series and the characterization of the subject soil is a corresponding soil classification.

6. The method of claim 5, wherein the determining includes computing for the second digital signature a closest matching signature from among the first digital signatures of the classified soils, the classification for the second geographic location being determined as the predefined reference soil series of the closest matching signature.

7. The method of claim 6, wherein the closest matching signature is computed by curve comparison.

8. The method of claim 1, further comprising storing the first digital signatures in a database.

9. The method of claim 1, wherein the first and second depth varying outputs of the plurality of sensors of the sensing tool are recorded continuously in a given timeframe.

10. The method of claim 1, wherein the sensing tool is a multi-sensor penetrometer.

11. The method of claim 1, wherein each predefined and known classification of the classified soils and the characterization of the subject soil are a level of classification chosen from a Soil Taxonomy classification system.

12. The method of claim 1, wherein each first digital signature is created for a combination of at least two of the first depth varying raw signal outputs, and the second digital signature is created for a combination of at least two of the second depth varying raw signal outputs.

13. A system for characterizing soil properties of a subject soil located in an unmapped, wrongly mapped, or minimally mapped geographic location, wherein the subject soil does not have an associated or correct predefined and known soil classification, the system comprising at least one processor configured to perform the method of claim 1.

14. The system of claim 13, wherein each first digital signature is created for a combination of at least two of the first depth varying raw signal outputs, and the second digital signature is created for a combination of at least two of the second depth varying raw signal outputs.

15. The system of claim 13, wherein the characterization of the subject soil comprises a first soil classification.

16. The system of claim 13, wherein each predefined and known soil classification is a reference soil series and the characterization of the subject soil is a corresponding soil classification.

17. The system of claim 16, wherein the determining includes computing for the second digital signature a closest matching signature from among the first digital signatures of the classified soils, the classification for the second geographic location being determined as the predefined reference soil series of the closest matching signature.

18. The system of claim 13, wherein the sensing tool is a multi-sensor penetrometer.

19. The system of claim 13, wherein each predefined and known classification of the classified soils and the characterization of the subject soil are a level of classification chosen from a Soil Taxonomy classification system.

* * * * *